United States Patent
Portolan et al.

(10) Patent No.: US 10,821,069 B2
(45) Date of Patent: Nov. 3, 2020

(54) AQUEOUS EXTRACT OF TRUFFLE AND COSMETIC COMPOSITION THEREOF

(71) Applicants: ISP INVESTMENTS LLC, Wilmington, DE (US); ELC MANAGEMENT LLC, Melville, NY (US)

(72) Inventors: Frédérique Portolan, Valbonne (FR); Valerie Lequoy, Valbonne (FR); Jean-Marie Botto, Valbonne (FR); Joel Mantelin, Cannes (FR); Isabelle Imbert, Cannes (FR); Nouha Domloge, Opio (FR); Noelle Garcia, Magagnosc (FR); Nadine A. Pernodet, Huntington Station, NY (US); Kelly Dong, Merrick, NY (US); Edward Pelle, Valley Stream, NY (US); Carl Haney, New York, NY (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 15/324,299

(22) PCT Filed: Jul. 7, 2015

(86) PCT No.: PCT/US2015/039304
§ 371 (c)(1),
(2) Date: Jan. 6, 2017

(87) PCT Pub. No.: WO2016/007461
PCT Pub. Date: Jan. 14, 2016

(65) Prior Publication Data
US 2017/0202773 A1    Jul. 20, 2017

Related U.S. Application Data

(60) Provisional application No. 62/021,789, filed on Jul. 8, 2014.

(51) Int. Cl.
| | |
|---|---|
| *A61Q 17/04* | (2006.01) |
| *A61Q 19/08* | (2006.01) |
| *A61K 8/9728* | (2017.01) |
| *A61K 8/9789* | (2017.01) |
| *A61K 8/9794* | (2017.01) |

(52) U.S. Cl.
CPC .......... *A61K 8/9728* (2017.08); *A61K 8/9789* (2017.08); *A61K 8/9794* (2017.08); *A61Q 17/04* (2013.01); *A61Q 19/08* (2013.01); *A61K 2800/85* (2013.01)

(58) Field of Classification Search
None
See application file for complete search history.

(56) References Cited

U.S. PATENT DOCUMENTS

| | | |
|---|---|---|
| 2004/0009143 A1 | 1/2004 | Golz-Berner et al. |
| 2010/0279946 A1 | 11/2010 | Dal Farra et al. |
| 2012/0093745 A1 | 4/2012 | Dal Farra et al. |
| 2012/0094921 A1 | 4/2012 | Dal Farra et al. |

OTHER PUBLICATIONS

PCT, International Search Report, International Application No. PCT/US2015/039304, 2 pages, dated Oct. 7, 2015.
PCT, Written Opinion of the International Searching Authority, International Application No. PCT/US2015/039304, 8 pages, dated Oct. 7, 2015.
Harman, D., "Aging: A Theory Based on Free Radical and Radiation Chemistry," J. Gerontol, 11, pp. 298-300 (1992).
Porteous, W.K. et al., "Bioenergetics consequences of accumulating the common 4977-bp mitochondrial DNA deletion," Eur. J. Biochem., 257, pp. 192-201 (1998).
Gabella, S. et al., "Transcript Profiling Reveals Novel Marker Genes Involved in Fruiting Body Formation in *Tuber borchii*," Eukaryotic Cell, vol. 4, No. 9, pp. 1599-1602 (2005).
Tang, Y. et al., "Comparison of sterol composition between *Tuber* fermentation mycelia and natural fruiting bodies," Food Chemistry, 132, pp. 1207-1213 (2012).
Splivallo, R. et al., "Discrimination of truffle fruiting body versus mycelial aromas by stir bar sorptive extraction," Phytochemistry, 68, pp. 2584-2598 (2007).

*Primary Examiner* — David J Blanchard
*Assistant Examiner* — Sarah J Chickos
(74) *Attorney, Agent, or Firm* — Thompson Hine LLP (57) ABSTRACT

The invention relates to a Truffle extract for skin cosmetic use, comprising compounds having a molecular weight of less than 5 kDa. The invention also relates to a cosmetic method of treatment designed to reduce and/or correct the signs of aging and photo-aging of the skin and keratinous appendages, and to protect the skin against aggressions due to ultraviolet radiation.

17 Claims, 5 Drawing Sheets

Figure 1: Effect of Truffle extract according to example 1 on mitochondrial Reactive Oxygen Species production n=3 +/- sem. (NS: non significant; *: significant; ***: highly significant) according to t test.

Figure 2: Effect of Truffle extract according to example 2 on mitochondrial Reactive Oxygen Species production after treatment with rotenone n=3 +/- sem. (NS: non significant; : very significant; *: highly significant) according to t test.

Figure 3: Effect of Truffle extract according to example 1 on mitochondrial Reactive Oxygen Species production after treatment with ultraviolet B radiations Figure 4: Effect of Truffle extract according to example 1 on ATP levels in Fibroblasts after treatment with ultraviolet A radiations.

Figure 5: Effect of Truffle extract according to example 1 on viability of Fibroblasts after treatment with ultraviolet A radiations.

AQUEOUS EXTRACT OF TRUFFLE AND COSMETIC COMPOSITION THEREOF

CROSS-REFERENCE TO RELATED APPLICATIONS

This application is the national stage entry of International Patent Application No. PCT/US2015/039304 filed on Jul. 7, 2015, which claims priority to U.S. Provisional Application No. 62/021,789 filed on Jul. 8, 2014, which are incorporated herein by reference in their entireties.

TECHNICAL FIELD

The present invention is in the field of cosmetics and more specifically in the field of skin care. The invention relates to a Truffle extract and cosmetic composition comprising a truffle extract.

The invention also relates to a cosmetic method of treatment designed to reduce and/or correct the signs of aging and photo-aging of the skin and keratinous appendages, and to protect the skin against aggressions due to ultraviolet radiation.

The Truffle extract can be used alone or in combination with other active agents.

BACKGROUND

The skin is a vital organ composed of several layers (dermis, proliferative layers and stratum corneum), which covers the entire surface of the body and ensures protective, sensitive, immune, metabolic or thermoregulatory functions. The skin, like the other organs, is subject to aging.

For example, the appearance of the skin is modified by various types of internal (disease and hormonal changes such as pregnancy) or external aggressions (environmental factors, such as pollution, sunlight, pathogens, etc.). Then wrinkles and fine lines, hyperpigmentation or hypopigmentation blemishes, dryness or even dehydration of the skin, thinning of the epidermis, elastosis, imperfections, age spots, etc., may appear. All of these changes affect not only the skin, but also the keratinous appendages such as the nails and hair.

It is known that free radicals, chemically unstable and very reactive species generated by the intracellular metabolism or external aggressions, play a key role in the aging process and more particularly in the formation of oxidized, damaged proteins (Harman et al. "Aging: a theory based on free radical and radiation chemistry" J. Gerontol., 11, 298-300). These external aggressions can include: ultraviolet radiation, toxins, atmospheric pollutants, alimentary oxidants. Ultraviolet radiations skin exposure induces extensive generation of reactive oxygen species (ROS). These can react with DNA, proteins, fatty acids and saccharides causing oxidative damage.

In the skin, premature aging is observed, occurring in the areas exposed to ultraviolet radiation, characterized by phenomena of alteration to the macromolecules (lipidic peroxidation, carbonylation of proteins), affecting in particular elastin, collagen or fibronectin.

One of the important consequences of the accumulation of oxidative damage is a reduction in the capacity of the cell to produce ATP (Porteous et al., Eur J Biochem 1998, 257(1): 192-201). Thus, the phenomenon of cellular aging is in relation to the oxidative damage which the cell undergoes, but also to the process of energy production necessary for the cell to survive.

It is known that fungi are a wide family of living organisms. Fruiting bodies of some wild and cultivatable mushrooms contain medicinal compounds which are being used in traditional medicines and cosmetics. Fungi have developed during their evolution various properties to resist environmental stress and it is known that some fungi compounds can have an effect to moderate damages caused by life circumstance and natural environment on organisms. Thus, research for new natural bioactive compounds from fungi origin has intensified.

For example, *Inonotus obliquus* mushroom contains enzyme such as Superoxide Dismutase (SOD), which is a key element in protecting the cell against ROS.

Also, truffles are known to be effective on certain conditions such as the improvement of immunity and hyperlipidemia.

The genus *Tuber* belongs to *Ascomycete phylum* and is subterranean fungus. The *Tuber* fungi genus comprises some species of truffles. These truffle species are hypogeous fungi that establish an ectomycorrhizal symbiosis with trees and shrubs and form a fruiting body.

Some of the truffle species are highly prized as a food, due to their fruiting bodies characteristic aroma and delicious taste. These species are referred to by "truffles" or "real truffles" and they are precious and expensive delicacies which are widely used in the famous French and Italian cuisines.

In the description of the invention "Truffles" refers to the following species: black truffle (also known as Perigord truffles from France, scientific name: *Tuber melanosporum*), the Italian white truffles (scientific name: *Tuber magnatum pico*), the Burgundy truffle (*Tuber uncinatum*), Kalahari truffle (*Terfezia pfeilii*), Lion-Truffle (*Trefezia leonis*), summer truffle (*Tuber aestivum*), winter truffle (*Tuber brumale*), Chinese Truffle (*Tuber sinensis* or *Tuber indicum*) and Bianchetto or whitish truffle (*Tuber borchii*).

In spite of the various anti-aging cosmetic products on the market for the treatment of skin, there remains a need for effective topically applied cosmetic compositions that provide anti-aging or rejuvenating benefits to the skin, hair and/or nails using natural ingredients as active agent. Unnatural, chemically-synthesized products may be perceived as being environmentally or personally unsafe. In contrast, natural products are perceived as pure, mild, and superior to chemically synthesized products. Numerous natural based products extracted from plants or herbs are known to contain antioxidant/free-radical scavenging agents that can neutralize the effects of free-radical damage. Additionally, they can contain agents that stimulate the synthesis and restoration of damaged connective tissue structures in the dermis and barrier function in the epidermis.

SUMMARY

The aim of the present invention is to provide a new extract of natural origin for the cosmetic industry which is always in demand of new active ingredients.

To this aim, the present invention proposes a Truffle extract for cosmetic treatment of the skin and/or appendages.

More specifically according to the invention, Truffle extract is obtained from fruiting bodies of *Tuber melanosporum*.

The inventors have now shown an aqueous extract of truffles (*Tuber Melanosporum*) is an active cosmetic agent capable of decreasing the production of mitochondrial reactive oxygen species (ROS), increasing the Adenosine Triphospate (ATP) production and increasing cellular viability after an external stress such as ultraviolet radiation exposure for example.

DETAILED DESCRIPTION

The main object of the present invention is a novel truffle aqueous extract for cosmetic use, comprising compounds having a molecular weight of less than 5 kDa.

"truffles" in the present invention refers to the truffle species of the genus *Tuber* highly prized as a food, due to their fruiting bodies characteristic aroma and delicious taste. Truffles include for example: black truffle (also known as Perigord truffles from France, scientific name: *Tuber melanosporum*), the Italian white truffles (scientific name: *Tuber magnatum* pico), the Burgundy truffle (*Tuber uncinatum*), Kalahari truffle (*Terfezia pfeilii*), Lion-Truffle (*Trefiza leonis*), summer truffle (*Tuber aestivum*), winter truffle (*Tuber brumale*), Chinese Truffle (*Tuber sinensis* or *Tuber indicum*) and Bianchetto or whitish truffle (*Tuber borchii*).

Skin refers to all of the covering tissue constituting the skin, the mucous membranes and the skin appendages, including hair, eyelashes and eyebrows.

It is clear that the invention is designed for mammals in general, and more specifically for human beings.

The inventors have indeed identified biological activities which are useful to reduce and/or correct the cutaneous signs of aging and photo-aging of the skin and keratinous appendages, and to protect the skin against aggressions due to ultraviolet radiation.

"Cutaneous signs of aging and photo-aging" refers to all changes in the external appearance of the skin and skin appendages due to aging, such as, for example, thinning of the skin, sagging, loss of hydration and atonia, deep wrinkles and fine lines, loss of firmness and tone, dermal atrophy or any other internal degradation of the skin resulting from exposure to ultraviolet radiation, liver spots and age spots. Liver spots also known as "Solar lentigo", "Lentigo senilis", "Old age spot", "Senile freckle", are blemishes on the skin associated with aging and photo-aging due to exposure to ultraviolet radiation from the sun. They range in color from light brown to red or black and are located in areas most often exposed to the sun, particularly the hands, face, shoulders, arms and forehead, and the scalp if bald.

The biological activities of the Truffle extract according to the invention are defined in vitro by the capacity of the aqueous extract of Truffles to decrease the production of mitochondrial reactive oxygen species (ROS) increasing the Adenosine Triphospate (ATP) production and increasing cellular viability after an external stress such as ultraviolet radiation exposure for example.

"Aqueous extract" is understood to be a mixture of compounds obtained by extraction with water.

"Topical application" is understood to be the application or spreading of a composition containing said truffle extract, on the surface of the skin or a mucus membrane.

It is understood by "physiologically acceptable" that the active agent according to the invention, or a composition containing said agent, is suitable for coming into contact with the skin or a mucus membrane without provoking a toxicity or intolerance reaction.

The active agent according to the invention can be obtained by aqueous extraction, followed by enzymatic hydrolysis which releases biologically active compounds. Preferably the enzymatic hydrolysis is performed with enzymes selected among carbohydrases and proteases.

A large number of compounds found in truffles are likely to have biologically activity. The controlled hydrolysis enables these compounds to be released.

In preferred embodiments the Truffle extract is obtained from *Tuber* species, and more preferably from *Tuber Melanosporum* and more preferably the Truffle extract is obtained from truffles fruiting body.

Truffles are Hypogeous fungi. During their evolution truffles lost the ability to disperse their spores via air currents, instead propagating by animal consumption and subsequent dispersal of their spores. The term "truffle fruiting body" refers to the truffle hypogeous ascocarps which is a multicellular structure on which spore-producing structures are borne. The fruiting body is part of the sexual phase of the fungal life cycle, with the rest of the life cycle being characterized by vegetative mycelial growth and asexual spore production.

Since truffle fruiting bodies cannot yet be obtained under in vitro controlled conditions, our knowledge of the morphogenetic events leading to ascocarp development and maturation as well as their underlying molecular bases, is quite limited. Changes in gene expression during the formation of the fruiting bodies have been described (Gabella et al., 2005). Furthermore, truffle mycelium and truffle fruiting body are considered as two distinct compartments, and are known to have a distinct composition and content (Tang et al., Food Chemistry 132 (2012) 1207-1213; Splivallo et al., Phytochemistry 68 (2007) 2584-2598).

One of the advantages of the present embodiment is that the fruiting bodies from truffles harvested at maturation are highly enriched in different compounds of interest compared to natural mycelium or in vitro grown mycelium.

All methods of aqueous extraction or purification known to the person skilled in the art can be used for the preparation of the extract according to the invention.

In a first stage, the truffles material is grounded in water and macerated in water.

The water extraction can be carried out at room temperature or with heated water between 40 and 90° C.

In a preferred embodiment the extraction is carried out by maceration in water heated at 50° C. for 2 hours.

This raw solution is then hydrolyzed under controlled conditions to produce soluble compounds.

According to the invention, hydrolysis is carried out either chemically or advantageously by carbohydrases or cellulases and proteases. The use of carbohydrases (for example VISCOZYM®: multi-enzymes complex containing a wide range of carbohydrases, including arabanase, cellulase, β-glucanase, hemicellulase, and xylanase; GLUCANEX®: a beta glucanase extracted from yeast (*Trichoderma harzianum*)), endoproteases produced by plants (papain, bromelain, ficin) and by micro-organisms (*Aspergillus, Rhizopus, Bacillus* etc.) can therefore be cited here.

Hydrolysis can be carried out with several enzymes at the same time or one hydrolysis step after another with one enzyme at once.

In preferred embodiments a first hydrolysis is carried out between 1 an 2 hours at a temperature between 40 and 80 degrees Celsius, and pH between 3 and 6 with between 1 and 10% carbohydrase enzyme.

In a particularly preferred embodiment, the first hydrolysis is carried out 2 hours at 55° C., pH between 4.5 and 5 with 4% VISCOZYME® or GLUCANEX®.

In preferred embodiments a second hydrolysis is carried out between 1 an 2 hours at a temperature between 40 and 80 degrees Celsius, and pH between 3 and 6 with between 1 and 10% endoprotease enzyme.

In a particularly preferred embodiment, the second hydrolysis is carried out 2 hours at 55° C., pH between 4.5 and 5 with 2% Bromelaine.

After hydrolysis steps, the obtained solution is unclear. To eliminate the residues, centrifugation and filtrations are carried out. Successive filtrations using filters with decreasing porosity are carried out. The obtained filtrate is a clear and brilliant solution.

Then a step of enzyme deactivation is carried out. Preferably enzymes are thermally deactivated, for example by heating the obtained filtrate between a couple of hours to one night at a temperature between 40 and 90° C., preferably 80° C.

After thermal deactivation of the enzymes, additional filtrations can optionally be done, to further remove the residual enzymes, and to select compounds with a low molecular weight.

After deactivation and removal by filtration, almost all the enzymes are eliminated from the filtrate. Thus a first active filtrate is obtained.

The advantage is the obtained active filtrate is free of residual enzymes which could be irritating or allergenic for the skin. Indeed proteolytic enzymes, such as papaïne, are known to be highly irritating if applied on the skin.

After clarification, and enzyme deactivation charcoal is added to the filtrate.

Indeed it is known truffle extracts emits odorant volatile compounds displeasing for a cosmetic application. Charcoal advantageously absorbs these odorant volatile compounds.

For example, charcoal SX plus (NORIT®) is added, preferably in a concentration from 0.1% to 1%, more preferably in a concentration of 0.25% to 0.5% for 30 minutes at room temperature to remove the odor.

Advantageously these ranges of concentration significantly decrease the displeasing odor of the extract without having part of the active molecules absorbed by the charcoal.

The filtrate is then diluted at a concentration between 3 g/Kg and 10 g/Kg, preferably at 5 g/Kg of dry matter with solvents, such as water, glycerol, ethanol, propanediol, butylene glycol, dipropylene glycol, ethoxylated or propoxylated glycols, cyclic polyols or any mixture of these solvents, for example 30% glycerol and 0.5% sodium benzoate.

Then, optionally, the diluted active agent is sterilized by sterile filtration, for example for one night in the oven at 65° C.

The extract obtained according to the invention is qualitatively and quantitatively analyzed.

The characteristics are the following:
Proteins: <2 g/kg
Sugars: around 1-3 g/kg
Amino acids: 1-2 g/kg
Phenolic compounds 0.1-0.3 g/Kg Thin layer chromatography an analysis showed that our final extract comprises expected amino acids according to what has been described in the truffle, more particularly in *Tuber Melanosporum*.

SDS PAGE electrophoresis showed that the extract obtained is composed of peptides with a molecular weight of less than 5 kDa.

Advantageously, the controlled hydrolysis enables access to molecules of interest from the Truffles fruiting body. The extract according to the invention is a Truffles extract enriched in compounds of interest and enriched in newly formed compounds from the lysis of native proteins and carbohydrates.

The extract according to the invention, comprises compounds with a molecular weight of less than 5 kDa. The advantage of the extract according to the invention is that small compounds are more stable and reproducible without having an allergenic effect After this dilution stage, the active agent can be encapsulated or introduced in a cosmetic or pharmaceutical carrier such as liposomes or any other microcapsule used in the field of cosmetics or adsorbed onto powdery organic polymers or mineral supports such as talc and bentonites.

The second aspect of the invention is a cosmetic composition comprising Truffles extract obtained by aqueous extraction and controlled hydrolysis, wherein compounds have a molecular weight of less than 5 kDa.

In preferred embodiment, the cosmetic composition comprises a Truffle extract from *Tuber Melanosporum*.

The composition according to the invention can be applied in any appropriate manner, in particular orally, parenterally or topically, and the formulation of the compositions will be adapted by the person skilled in the art, in particular for cosmetic or dermatological compositions. The compositions according to the invention are advantageously designed to be administered topically. These compositions must therefore contain a physiologically acceptable medium, i.e. compatible with the skin and epithelial appendages, and cover all cosmetic or dermatological forms.

According to an advantageous embodiment of the invention, the active agent according to the invention is present in the compositions of the invention in an effective quantity that is to say in a concentration of between approximately 0.0001% and 20% and preferably in a concentration of between approximately 0.001% and 5% relative to the total weight of the final composition.

These compositions can specifically exist in the form of an aqueous, hydroalcoholic or oily solution; oil-in-water emulsion, water-in-oil emulsion or multiple emulsions; these can also exist in the form of creams, suspensions or even powders adapted for application on the skin, mucus membranes, lips and/or epithelial appendages. These compositions can also be more or less fluid and have the appearance of a cream, a lotion, milk, a serum, pomade, a gel, a paste or a mousse. They can also exist in solid form, as a stick, or can be applied to the skin as an aerosol. They can also be used as a skincare product and/or as a makeup product.

Furthermore, the composition comprises any conventionally used additive envisaged in the scope of application as well as necessary additives for their formulation, such as co-solvents (ethanol, glycerol, benzyl alcohol, damper . . . ), thickeners, thinners, emulsifiers, antioxidants, colorants, solar filters, pigments, fillers, preservatives, perfumes, odor absorbers, essential oils, oligoelements, essential fatty acids, surfactants, film-forming polymers, chemical filters or minerals, moisturizing agents or thermal waters etc. Water-soluble, preferably natural, polymers, such as polysaccharides or polypeptides, cellulose derivatives of the type methylcellulose or hydroxypropylcellulose, or even synthetic polymers, poloxamers, carbomers, siloxanes, PVA or PVP, and in particular polymers sold by the company Ashland, can be cited, for example.

In every instance, the person skilled in the art will ensure that these additives and proportions thereof are selected in such a way as to not be detrimental to the desired advantageous properties of the composition according to the invention. These additives can, for example, be present in concentrations from 0.01% to 20% of the total weight of the composition. When the composition of the invention is an emulsion, the fatty phase can represent from 5 to 80% in weight, and preferably from 5 to 50% in weight relative to the total weight of the composition. The emulsifiers and co-emulsifiers used in the composition are to be selected from those which are typically used in the relevant field. For example, they can be used in a proportion from 0.3 to 30% in weight, relative to the total weight of the composition.

It is well understood that the active agent according to the invention can be used on its own or in conjunction with other active ingredients.

Furthermore, the compositions which can be used according to the invention advantageously contain at least one other active agent. The following types of ingredients can be cited, in a non-limiting manner: other peptide active agents, vegetable extracts, healing agents, anti-aging agents, anti-wrinkle agents, soothing agents, anti-free radicals, anti-ultraviolet radiation agents, agents for stimulating dermal macromolecular synthesis or energetic metabolism, moisturizing agents, antibacterial agents, antifungal agents, anti-inflammatories, anesthetics, agents modulating cutaneous differentiation, cutaneous pigmentation or depigmentation, and agents for stimulating nail and hair growth.

It is preferable for an anti-free radical or antioxidant agent, or an agent stimulating dermal macromolecular synthesis or energetic metabolism, to be used.

In a more specific embodiment, the composition according to the invention will comprise, in addition to the Truffle extract according to the invention:
- sunscreens, ultraviolet and Infrared screens
- anti-free radical agents,
- DHEA (dehydroepiandrosterone),
- at least one cytochrome c-activating compound, and/or;
- one (or more) aquaporin-activating compound and/or;
- one (or more) sirtuin-activating compound and/or;
- one (or more) compound that increases cell adhesion and/or;
- one (or more) compound that increases the production of matrix proteins of the collagen or laminin type, etc.;
- one (or more) HSP protein-modulating compound;
- one (or more) compound that increases cell energy;
- one (or more) pigmentation-modulating compound such as a yeast, amaranth, linseed, bean, cacao, corn, soy, sunflower, rapeseed or pea peptide extract;
- one (or more) compound improving the skin barrier function;
- one (or more) mitochondria-protecting compound.
- vitamin A and notably retinoic acid, retinol, retinol propionate, retinol palmitate,
- vitamin B3 and notably niacinamide, niconitate of tocopherol,
- vitamin B5, vitamin B6, vitamin B12, panthenol,
- vitamin C, and notably ascorbic acid, ascorbyl glucoside, ascorbyl tetrapalmitate, magnesium and sodium ascorbyl phosphate,
- vitamins E, F, H, K, PP, and coenzyme Q10,
- metalloproteinase inhibitor, activator of Tissue Inhibitor Metalloproteinase (TIMP),
- aminoacids and notably arginine, ornithine, hydroxyproline, hydroxyproline dipalmitate, palmitoylglycine, hydroxylysine, methionine and its derivatives, N-acylated aminoacids,
- natural or synthetic peptides, including, di-, tri-, tetra-, penta- and hexapeptides and their lipophilic derivatives, isomers and complex with other molecules such as metallic ion (i.e. copper, zinc, manganese, magnesium, and others), peptides sold under commercial names MATRIXYL®, ARGIRELINE®, COL-LAXYL™, PEPTIDE VINCI 02™ CHRONOGEN™, LAMINIXYL IS™, PEPTIDE Q10™,
- peptidic plant extracts obtained by hydrolysis or any other methods such as soy extract, einkorn extract, *Vitis vinifera* extract, rapeseed extract, flaxseed extract rice extract, corn extract, or pea extract, carob extract, bean extract, fava extract,
- yeast extract, artemia salina extract,
- dehydroacetic acid (DHA),
- natural or synthetic phystosterols,
- alpha- and beta-hydroxyacids, silanols,
- sugar amines, glucosamine, D-glucosamine, N-acetyl-glucosamine, N-acetyl-D-glucosamine, mannosamine, N-acetyl mannosamine, galactosamine, N-acetyl galactosamine,
- polyphenols, isoflavones, flavonoids, such as grap extract, pine extract, olive extract,
- lipids such as ceramides or phospholipids,
- animal oils such as squalenes or squalanes,
- vegetal oils, such as almond oil, coconut oil, castor oil, jojoba oil, olive oil, rapeseed oil, peanut oil, sunflower oil, wheat germ oil, corn germ oil, soybean oil, cotton oil, alfalfa oil, poppy oil, pumpkin seed oil, evening primrose oil, millet oil, barley oil, rye oil, safflower oil, passion oil, hazelnut oil, palm oil, apricot kernel oil, avocado oil, calendula oil, ethoxylated vegetable oils, or shea butter. The abovementioned compounds can be natural, such as peptide hydrolysates of plants, or also synthetic, such as peptide compounds.

The third aspect of the invention is a cosmetic method for reducing and/or correcting the signs of aging and photo-aging of the skin and keratinous appendages, comprising topically applying to the skin, the mucous membranes and/or skin appendages a composition comprising a Truffle extract according to the invention.

"Cutaneous signs of aging and photo-aging" refers to all changes in the external appearance of the skin and skin appendages due to aging, such as, for example, thinning of the skin, sagging, loss of hydration and atonia, deep wrinkles and fine lines, loss of firmness and tone, dermal atrophy or any other internal degradation of the skin resulting from exposure to ultraviolet radiation, liver spots and age spots.

The fourth object of the invention is a cosmetic method designed to protect the skin against aggressions due to ultraviolet radiation, wherein a cosmetic composition comprising a Truffle extract according to the invention is applied topically on the skin which is to be treated.

The fifth object of the invention is a cosmetic method designed to increase ATP levels in skin cells, wherein a cosmetic composition comprising a Truffle extract according to the invention is applied topically on the skin which is to be treated.

The sixth object of the invention is a cosmetic method designed to reduce ROS levels in skin cells, wherein a cosmetic composition comprising a Truffle extract according to the invention is applied topically on the skin which is to be treated.

The embodiments which are specific to this cosmetic method also result from the above description.

Further advantages and characteristics of the invention can be seen in greater detail by reading the illustrative, non-limiting examples provided.

EXAMPLE 1

Preparation of a Truffle extract (*Tuber melanosporum*)

100 g of black truffle (*Tuber melanosporum*) is grounded in 1 liter of water. 4% VISCOSYM® is added in the mixture and the solution is heated 2 hours at 50° C. VISCOZYM® is a multi-enzymes complex containing a wide range of carbohydrases, including arabanase, cellulase, β-glucanase, hemicellulase, and xylanase. Then, 2% bromelain is added in the solution and the mixture is heated 2 hours at 50-55° C. Then the enzyme is deactivated by heating the solution to 80° C. for 2 hours.

After centrifugation, the supernatant is filtered on filters with decreasing porosity. The purification process begins by successive filtrations using Seitz-Orion filters of decreasing porosity (up to 0.2 µm) so as to obtain a clear, bright solution.

After clarification, the filtrate is heated overnight at 65° C. and then charcoal (SX plus −0.25%) is added for 30 min at room temperature to remove the odor. The filtrate is then diluted to obtain an extract having 6 g/Kg dry matter with 30% glycerol and 0.5% sodium benzoate.

This solution is then purified by eliminating the enzymes and high molecular weight proteins using cross-flow filtration.

Truffle extract was analyzed using standard procedure. The characteristics of the Truffle extract obtained are the following: dry matter: 6 g/kg—proteins: <1 g/kg—sugars: 2 g/kg—amino acids: 1.4 g/kg—Phenolic compounds 0.1-0.3 g/Kg SDS PAGE electrophoresis (NuPAGE® Bis-Tris Pre-cast (Invitrogen)) was performed to assess molecular weight of proteins of the extract. The Truffle extract is heated to 70° C. for 10 minutes in reductive denaturing conditions in a NuPAGE® LDS sample buffer. A NuPAGE® Antioxidant solution is added to the inner chamber (cathode) so that the reduced proteins do not re-oxidize during electrophoresis. Protein migration is carried out using the NuPAGE® MES running buffer with standard SeeBlue Plus2 as a marker for molecular weight. Protein staining is carried out using Coomassie® Brilliant Blue R-250.

The extract obtained is composed of peptides with a molecular weight of less than 3.5 kDa.

EXAMPLE 2

Preparation of a Truffle Extract (*Tuber melanosporum*)

100 g of black truffle (*Tuber melanosporum*) is grounded in 1 liter of water. 4% GLUCANEX® is added in the mixture and the solution is heated 2 hours at 50° C. GLUCANEX® is a beta glucanase extracted from yeast (*Trichoderma harzianum*) Then, 2% bromelain is added in the solution and the mixture is heated 2 hours at 50-55° C. After centrifugation, the supernatant is filtered on filters with decreasing porosity.

After clarification, the filtrate is heated overnight at 65° C. and then charcoal (SX plus −0.25%) is added for 30 min at room temperature to remove the odor. The filtrate is then diluted to obtain an extract having 8 g/Kg dry matter with 30% glycerol and 0.5% sodium benzoate.

This solution is then purified by eliminating the enzymes and high molecular weight proteins using cross-flow filtration.

The next stage is the dilution phase in a water-glycerol mixture. The diluted active agent is then sterilized by sterile filtration.

Truffle extract was analyzed using standard procedure. The characteristics of the Truffle extract obtained are the following: dry matter: 8 g/kg—proteins: <1 g/kg—sugars: 6.9 g/kg—amino acids: 1.4 g/kg SDS PAGE electrophoresis (NuPAGE® Bis-Tris Pre-cast (Invitrogen)) was performed to assess molecular weight of proteins of the extract. The Truffle extract is heated to 70° C. for 10 minutes in reductive denaturing conditions in a NuPAGE® LDS sample buffer. A NuPAGE® Antioxidant solution is added to the inner chamber (cathode) so that the reduced proteins do not re-oxidize during electrophoresis. Protein migration is carried out using the NuPAGE® MES running buffer with standard SeeBlue Plus2 as a marker for molecular weight. Protein staining is carried out using Coomassie® Brilliant Blue R-250.

The extract obtained is composed of peptides with a molecular weight of less than 3.5 kDa.

EXAMPLE 3

Effect of Truffle Extract According to Example 1 on Mitochondrial Reactive Oxygen Species Production The purpose of this study is to determine the influence of the Truffle extract according to example 1 regarding the mitochondrial Reactive oxygen Species (ROS) production.

Method: Normal human keratinocytes extracted from a 52 years old European women abdominal skin were seeded in 8 well culture PERMANOX® plastic slides (Thermo Scientific, Waltham, Mass., USA). Cells were pre-treated with two applications per day of the Truffle extract according to example 1 (respectively at 0.01% and 0.05% for 48 h in KSFM medium (Gibco, Auckland, NZ) supplemented with 50 µg·ml-1 bovine pituitary extract (Gibco), 5 ng·ml-1 human recombinant EGF (Gibco) and 0.1 mg·ml-1 PRIMO-CIN™ (Invivogen, San Diego, Calif., USA). Culture medium was replaced with fresh KSFM for 1 hour. At the end of incubation, a 5 µM MITOSOX® (Life Technologies, Carlsbad, Calif., USA) solution was incubated further for 20 min at 37° C. in 5% CO2 atmosphere. Cells were washed three times in Hank's Balanced Salt Solution (Gibco), fixed with formaldehyde 3.7% (Sigma, Steinheim, Germany) for 20 minutes then nuclei were revealed by staining with a 0.3 µM DAPI solution (Life Technologies) for ten minutes. Digital images were acquired with an inverted Zeiss Axiovert 200M microscope (Zeiss, Oberkochen, Germany) with a 20× objective. Photos were taken with a Qimaging EXI blue camera (Qimaging, Surrey, BC, Canada) coupled to Volocity acquisition software (Perkin Elmer, Waltham, Mass., USA). All the values are represented as means±SEM. Statistical significance of the data was assessed by paired Student's t-test (n=3, p<0.05 was considered significant; p<0.01 as very significant and p<0.005 as highly significant).

Figure 1:
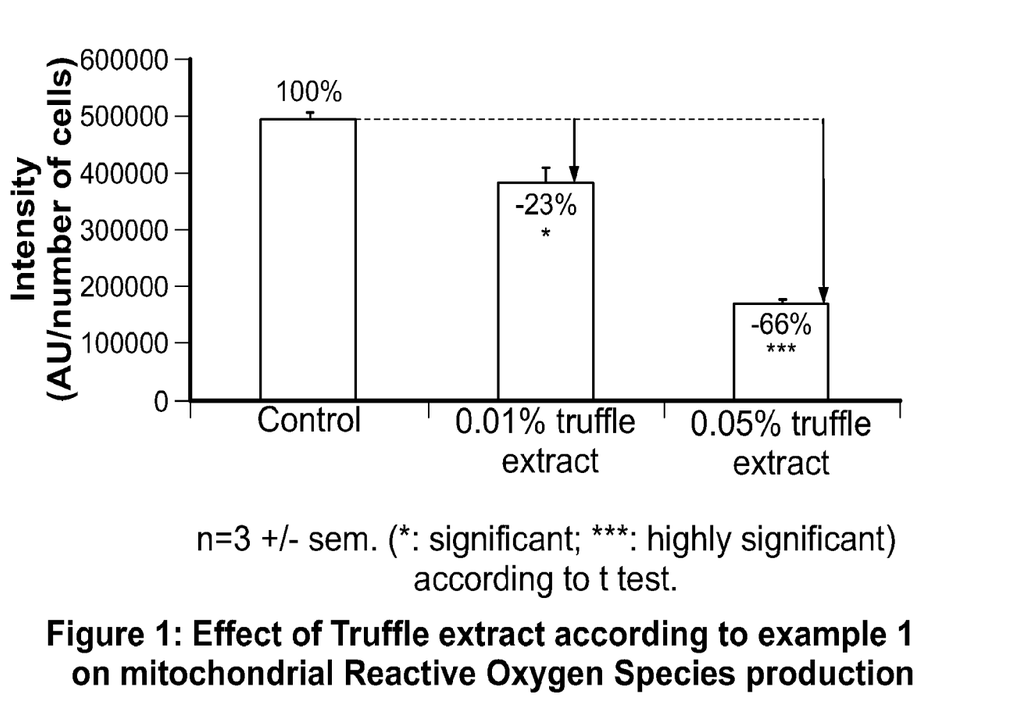
FIG. 1: Effect of Truffle extract according to example 1 on mitochondrial Reactive Oxygen Species production.

Results: As illustrated by FIG. 1, we observed a 23% decrease of ROS production in keratinocytes treated with 0.01% Truffle extract according to example 1, compared to untreated keratinocytes and a highly significant 66% decrease of ROS production in keratinocytes treated with 0.05% Truffle extract according to example 1, compared to untreated keratinocytes Conclusion: The Truffle extract according to example 1, decreases mitochondrial ROS levels in the skin.

EXAMPLE 4

Effect of Truffle Extract According to Example 2 on Mitochondrial Reactive Oxygen Species Production after Rotenone-Induced Production of ROS The purpose of this study is to determine the influence of the Truffle extract according to example 2 regarding the mitochondrial Reactive oxygen Species (ROS) production. Mitochondrial ROS were induced by rotenone, an electron transport chain complex inhibitor.

Method: Normal human keratinocytes extracted from a 52 years old European women abdominal skin were seeded in 8 well culture PERMANOX® plastic slides (Thermo Scientific, Waltham, Mass., USA). Cells were pre-treated with two applications per day of the Truffle extract of example 2 (at 0.01% and 0.05%) for 48 h in KSFM medium (Gibco, Auckland, NZ) supplemented with 50 µg·ml-1 bovine pituitary extract (Gibco), 5 ng·ml-1 human recombinant EGF (Gibco) and 0.1 mg·ml-1 PRIMOCIN™ (Invivogen, San Diego, Calif., USA). Then cells were submitted to 1 µM Rotenone application for 4 hours. Immediately after the stress, culture medium was replaced with fresh KSFM for 1 hour. At the end of incubation, a 5 µM MITOSOX® (Life Technologies, Carlsbad, Calif., USA) solution was incubated further for 20 min at 37° C. in 5% CO2 atmosphere. Cells were washed three times in Hank's Balanced Salt Solution (Gibco), fixed with formaldehyde 3.7% (Sigma, Steinheim, Germany) for 20 minutes then nuclei were revealed by staining with a 0.3 µM DAPI solution (Life Technologies) for ten minutes. Digital images were acquired with an inverted Zeiss Axiovert 200M microscope (Zeiss, Oberkochen, Germany) with a 20× objective. Photos were taken with a Qimaging EXI blue camera (Qimaging, Surrey, BC, Canada) coupled to Volocity acquisition software (Perkin Elmer, Waltham, Mass., USA). All the values are represented as means±SEM. Statistical significance of the data was assessed by paired Student's t-test (n=3, p<0.05 was considered significant; p<0.01 as very significant and p<0.005 as highly significant).

Figure 2:
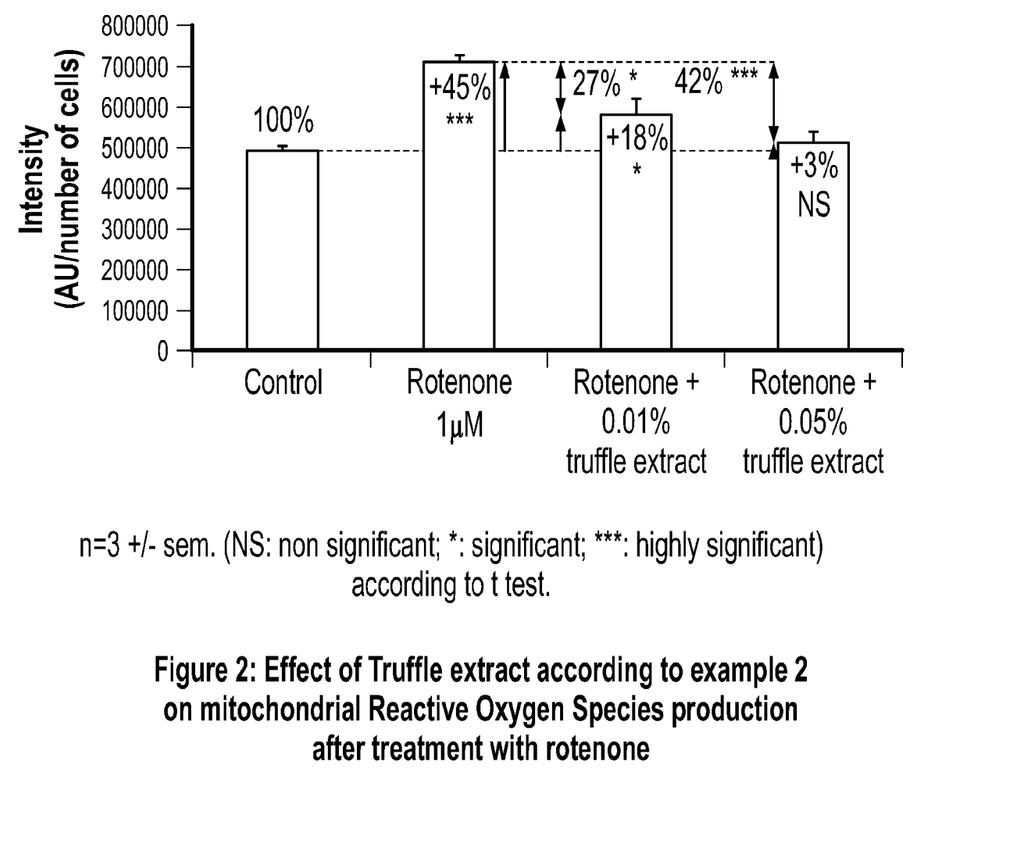
FIG. 2: Effect of Truffle extract according to example 2 on mitochondrial Reactive Oxygen Species production after treatment with rotenone.

Results: FIG. 2 shows the results. First we observed rotenone treatment produced a 45% increase in ROS production in keratinocytes, compared to untreated control.

We observed that the increase of ROS production in keratinocytes treated with 0.01% and 0.05% Truffle extract according to example 2 after rotenone treatment was respectively of 27% and 42% lower compared to keratinocytes untreated with the Truffle extract and treated with rotenone.

Conclusion: The Truffle extract according to example 1, effectively protects the skin from rotenone-induced mitochondrial production of ROS.

EXAMPLE 5

Effect of Truffle Extract According to Example 1 on Mitochondrial Reactive Oxygen Species Production after Ultraviolet B-Induced Production of ROS The purpose of this study is to determine the influence of the Truffle extract according to example 1 regarding the mitochondrial Reactive oxygen Species (ROS) production.

Method: Normal human keratinocytes extracted from a 52 years old European women abdominal skin were seeded in 8 well culture Permanox® plastic slides (Thermo Scientific, Waltham, Mass., USA). Cells were pre-treated with two applications per day of the Truffle extract (respectively at 0.01% and 0.05%) for 48 h in KSFM medium (Gibco, Auckland, NZ) supplemented with 50 µg·ml-1 bovine pituitary extract (Gibco), 5 ng·ml-1 human recombinant EGF (Gibco) and 0.1 mg·ml-1 PRIMOCIN™ (Invivogen, San Diego, Calif., USA). Then cells were submitted to 75 $mJ/cm^2$ UVB application for 4 hours. Immediately after the stress, culture medium was replaced with fresh KSFM for 1 hour. At the end of incubation, a 5 µM MITOSOX® (Life Technologies, Carlsbad, Calif., USA) solution was incubated further for 20 min at 37° C. in 5% CO2 atmosphere. Cells were washed three times in Hank's Balanced Salt Solution (Gibco), fixed with formaldehyde 3.7% (Sigma, Steinheim, Germany) for 20 minutes then nuclei were revealed by staining with a 0.3 µM DAPI solution (Life Technologies) for ten minutes. Digital images were acquired with an inverted Zeiss Axiovert 200M microscope (Zeiss, Oberkochen, Germany) with a 20× objective. Photos were taken with a Qimaging EXI blue camera (Qimaging, Surrey, BC, Canada) coupled to Volocity acquisition software (Perkin Elmer, Waltham, Mass., USA). All the values are represented as means±SEM. Statistical significance of the data was assessed by paired Student's t-test (n=3, p≤0.05 was considered significant; p≤0.01 as very significant and p≤0.005 as highly significant).

Figure 3:
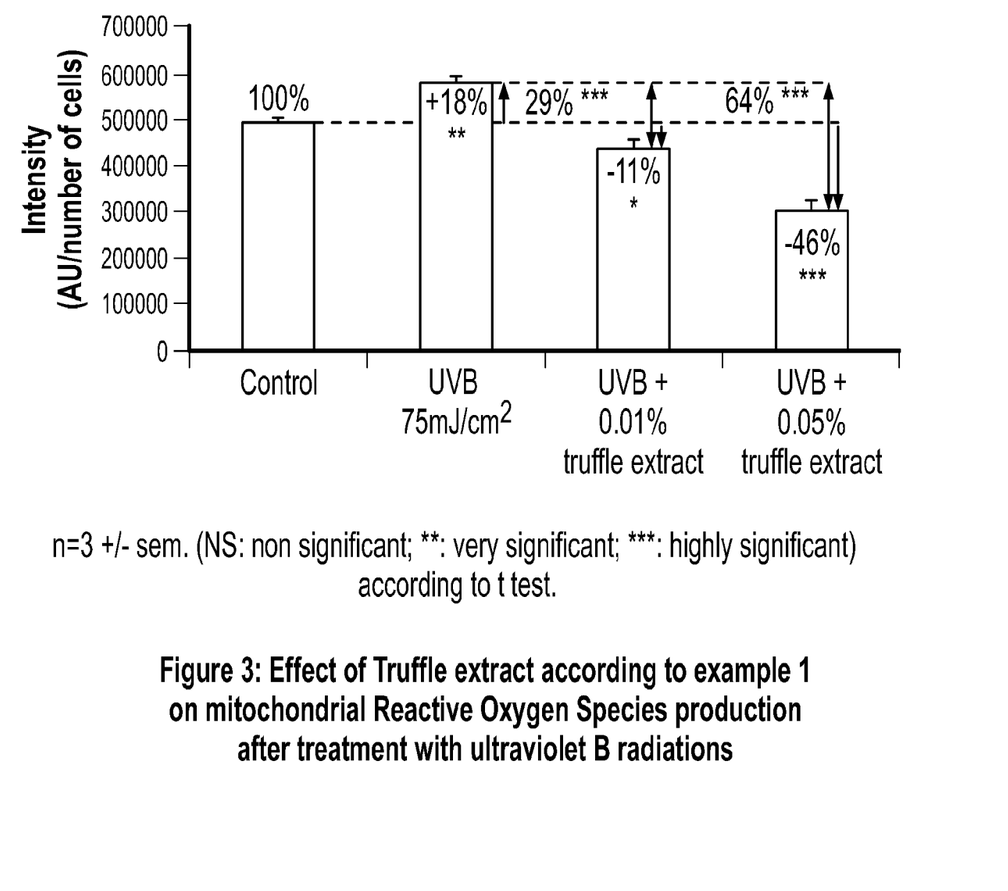
FIG. 3: Effect of Truffle extract according to example 1 on mitochondrial Reactive Oxygen Species production after treatment with ultraviolet B radiations.

Results: FIG. 3 shows the results. First we observed Ultraviolet B radiation induced stress produced a 18% increase in production of ROS in keratinocytes compared to untreated control.

We observed that the increase of ROS production in keratinocytes treated with 0.01% and 0.05% Truffle extract according to example 2 after rotenone treatment was 29% and 64% lower compared to keratinocytes untreated with the Truffle extract and ultraviolet B radiation.

Conclusion: The Truffle extract according to example 1, effectively protects the skin from ultraviolet B-induced mitochondrial production of ROS.

EXAMPLE 6

Effect of Truffle Extract According to Example 1 on ATP Levels in Fibroblasts

The purpose of this study is to determine the influence of the Truffle extract according to example 1 regarding the intracellular levels of Adenosine Triphosphate (or ATP).

Method: Normal human fibroblasts from a 62 yr-old donor are treated with the Truffle extract according to example 1 at 0.001% for 24 hours, irradiated by Ultraviolet A (10 J/cm$^2$) and then cultivated again 24 hours in the presence of the same concentration of Truffle extract according to example 1. Untreated and non-irradiated controls are carried out under the same conditions.

The ATP assay kit is an adenosine 5'-triphosphate (ATP) monitoring system based on firefly (Photinus pyralis) luciferase. This assay is used to determine the total levels of cellular ATP in culture. The ATP assay is based on the production of light caused by the reaction of ATP with added luciferase and D-luciferin. The emitted light is proportional to the ATP concentration inside the cell.

Prepare the substrate solution by reconstituting the lyophilized substrate solution of the ATP assay kit in 5 ml of substrate buffer solution. Wash cells with PBS then add 50 µl of lysis solution to each well and place plate on shaker for 5 min. Remove 20 µl from each well and place into the 96-well plate containing 20 µl of MICRO BCA™ Protein Assay working solution in each well. Add 50 µl of substrate solution to each well. Place plate on shaker for 5 min. Measure the luminescence with a luminometer.

Figure 4:
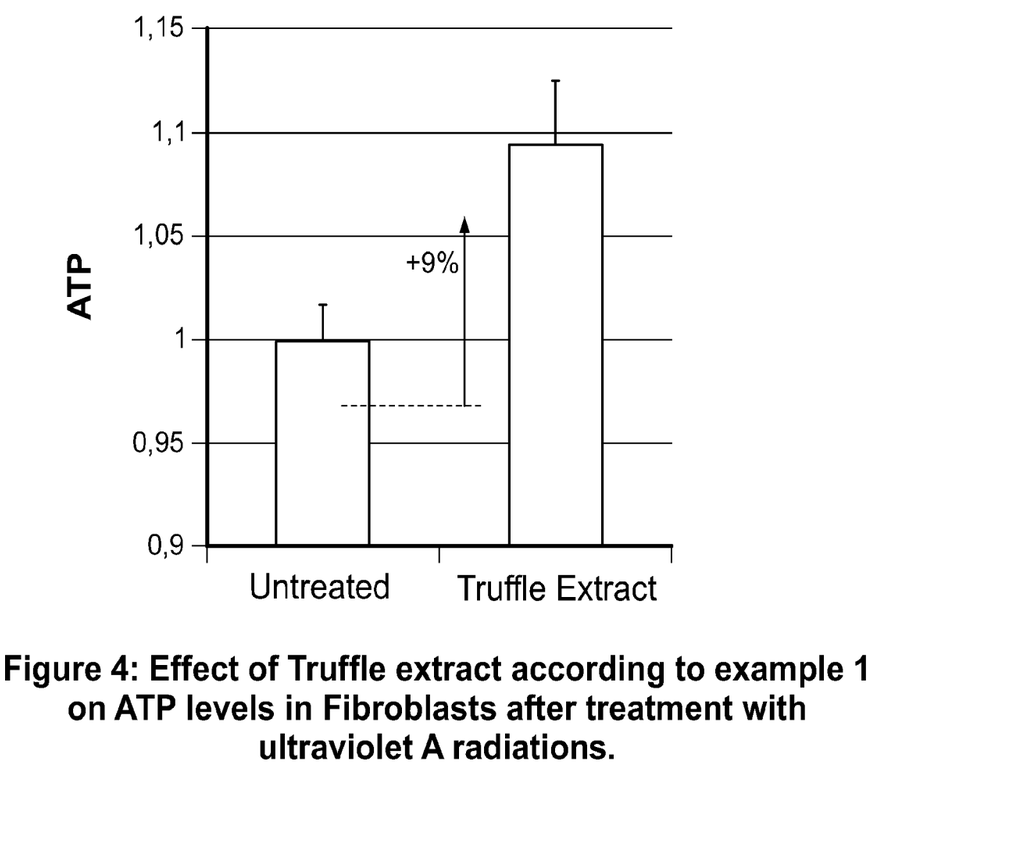
FIG. 4: Effect of Truffle extract according to example 1 on ATP levels in Fibroblasts after treatment with ultraviolet A radiations.

Results: FIG. 4 illustrates the results. We observed a 9% increase of ATP level in fibroblasts treated with 0.001% Truffle extract according to example 1 and irradiated with ultraviolet A, compared to untreated fibroblasts.

Conclusion: The Truffle extract according to example 1, effectively increases ATP level in the skin cells submitted to ultraviolet A stress.

EXAMPLE 7

Effect of Truffle Extract According to Example 1 on Fibroblasts Viability

The goal of this study is to determine the protective effect of the Truffle extract according to example 1 with relation to normal human fibroblasts subjected to stress by Ultraviolet A radiation.

To do this, cellular viability tests were conducted by the Alamar Blue Viability Assay Method: Normal human fibroblasts from a 62 yr-old donor are treated with the Truffle extract according to example 1 at 0.001% for 24 hours, irradiated by ultraviolet A (10 J/cm$^2$) and then cultivated again 24 hours in the presence of the same concentration of Truffle extract according to example 1.

Untreated and non-irradiated controls are carried out under the same conditions. At the end of the experiment, the cells are incubated in a 200 µl solution containing 10% of ALAMARBLUE® then incubated for 2 hours in the incubator and the fluorescence is read on a fluorescent plate reader at 530 nm excitation and 590 nm emission.

Resazurin, the active ingredient of ALAMARBLUE® reagent, is a non-toxic, cell permeable compound that is blue in color and virtually non-fluorescent. Upon entering cells, resazurin is reduced to resorufin, a compound that is red in color and highly fluorescent. Viable cells continuously convert resazurin to resorufin, increasing the overall fluorescence and color of the media surrounding cells. The fluorescence intensity is then directly proportional to the mitochondrial enzymatic activity as well as to the number of living cells.

Figure 5:
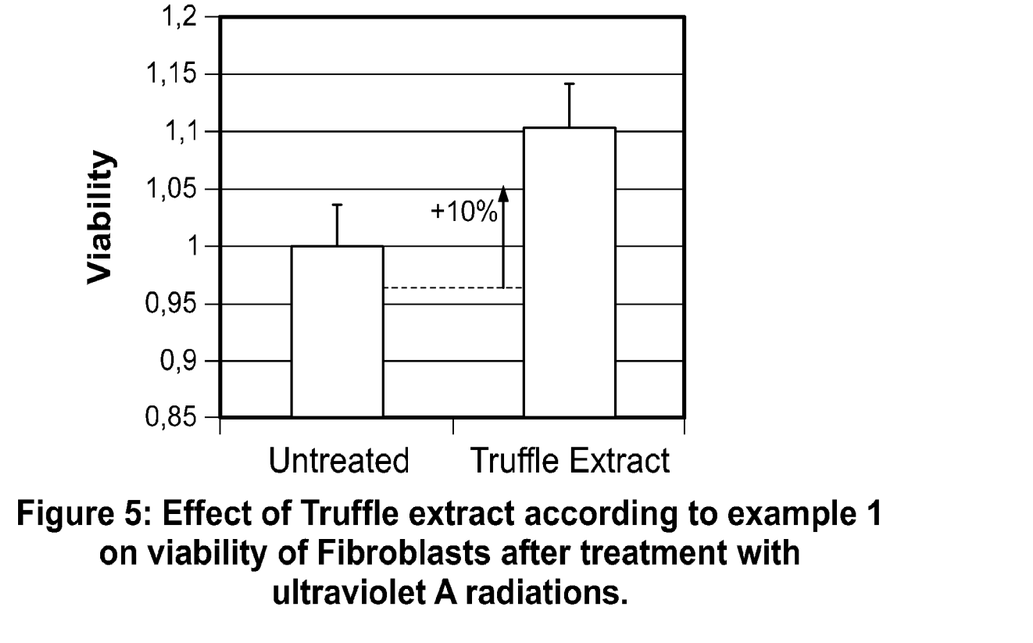
FIG. 5: Effect of Truffle extract according to example 1 on viability of Fibroblasts after treatment with ultraviolet A radiations.

Results: FIG. 5 illustrates the results. Evaluation of cellular viability by the Alamar Blue Viability Assay shows that the Truffle extract according to example 1 increases cellular viability after ultraviolet A irradiation by 10%.

Conclusion: The Truffle extract according to example 1 at 0.001% increases cellular viability and effectively protects the skin cells from the cytotoxic effects of ultraviolet A radiation.

EXAMPLE 8

Preparing the Compositions

1—Day Cream

| Trade Names | INCI Names | wt % |
|---|---|---|
| PHASE A | | |
| MONTANOV 68 | Cetearyl Alcohol (and) Cetearyl Glucoside | 5.00 |
| JOJOBA OIL | Simmondsia Chinensis (Jojoba) Seed Oil | 3.00 |
| VASELINE OIL | Paraffinum Liquidum (Mineral Oil) | 2.00 |
| SQUALANE | Squalane | 3.00 |
| CERAPHYL 368 | Ethylhexyl palmitate | 4.00 |
| CERAPHYL 41 | C12-C15 Alkyl Lactate | 3.00 |
| RAPITHIX A-60 | Sodium polyacrylate (and) Hydrogenated Polydecene (and) Trideceth -6 | 0.30 |
| PHASE B | | |
| GLYCERIN | Glycerin | 5.00 |
| ALLANTOIN | Allantoin | 0.10 |
| DEMINERALIZED WATER | Aqua (Water) | qs 100 |
| PHASE C | | |
| ROKONSAL MEP | Phenoxyethanol (and) Methylparaben (and) Ethylparaben (and) Propylparaben | 0.50 |
| PHASE D | | |
| ACTIVE AGENT OF EXAMPLE 1 | | 0.01 |
| PHASE E | | |
| FRAGRANCE | Perfume (Fragrance) | qs |

Operating Mode:

Weigh the ingredients of the fat phase and heat to 70° C. under stirring. Prepare phase B and heat to 70° C. Emulsify phase A into phase B. Add phase C at about 50° C. under stirring. Add the active agent below 40° C. (Phase D). Perfume and cool to room temperature.

2—Sun Protection Cream:

| Trade names | INCI names | Weight percent |
|---|---|---|
| PHASE A | | |
| Demineralized water | Aqua (Water) | qsp |
| Pemulen TR1 | Acrylates/C10-30 Alkyl Acrylate Crosspolymer | 0.40 |
| Glycerin | Glycerin | 3.00 |
| ROKONSAL MEP | Phenoxyethanol (and) Methylparaben (and) Ethylparaben (and) Propylparaben | 0.5 |
| PHASE B | | |
| ESCALOL ® 557 | Ethylhexyl Methoxycinnamate | 7.50 |
| ESCALOL ® 567 | Benzophenone-3 | 3.00 |
| ESCALOL ® 517 | Butyl Methoxydibenzoylmethane | 2.00 |

-continued

| Trade names | INCI names | Weight percent |
|---|---|---|
| Myritol 318 | Caprylic/Capric Triglycerides | 4.00 |
| Emulgade SEV | Hydrogenated Palm Glycerides (and) Ceteareth-20 (and) Ceteareth-12 (and) Cetearyl Alcohol | 5.00 |
| Nacol 16-98 | Cetyl Alcohol | 1.00 |
| PHASE C | | |
| TEA | Triethanolamine | 0.20 |
| PHASE D | | |
| ACTIVE AGENT OF EXAMPLE 2 | | 0.05 |
| Fragrance | Fragrance | qsp |
| Colorant | | qsp |

The constituents of phase A and phase B are heated separately between 70° C. and 75° C. Phase B is emulsified in phase A under stirring. Phase C is added at 45° C., by increasing the stirring. Phase D is then added when the temperature is below 40° C. The cooling is continued until 25° C. under intensive stirring.

3—Anti-Aging Cream:

| Trade names | INCI names | Weight percent |
|---|---|---|
| Phase A | | |
| Montanov 68 | Cetearyl Alcohol (and) Cetearyl Glucoside | 6.00 |
| Squalane | Squalane | 3.00 |
| Refined Shea Butter | *Butyrospermum Parkii* (Shea Butter) | 2.00 |
| Waglinol 250 | Cetearyl Ethylhexanoate | 3.00 |
| Amerchol L-101 | Mineral Oil (and) Lanolin Alcohol | 2.00 |
| SI-TEC ™ DM 350 | Dimethicone | 1.50 |
| BHT | BHT | 0.01 |
| Coenzyme Q10 | Ubiquinone | 0.10 |
| Phase B | | |
| Avocado oil | *Persea Gratissima* (Avocado) Oil | 1.25 |
| ROKONSAL MEP | Phenoxyethanol (and) Methylparaben (and) Ethylparaben (and) Propylparaben | 0.75 |
| Phase C | | |
| Demineralized water | Aqua (Water) | qsp |
| Butylene Glycol | Butylene Glycol | 2.00 |
| Glucam E10 | Methyl Gluceth-10 | 1.00 |
| Allantoin | Allantoin | 0.15 |
| Carbopol Ultrez 10 | Carbomer | 0.20 |
| Phase D | | |
| TEA | Triethanolamine | 0.18 |
| Phase E | | |
| ACTIVE AGENT OF EXAMPLE 1 | | 0.01 |
| GP4G | Water (and) Artemia Extract | 1.50 |
| COLLAXYL ® | Water (and) Butylene Glycol (and) Hexapeptide-9 | 3.00 |
| Phase F | | |
| Fragrance | Fragrance | qsp |
| Colorant | | qsp |

Prepare and melt phase A at 65-70° C. Heat phase C to 65-70° C. Phase B is added to phase A just before emulsifying AB into C. At approximately 45° C., the carbomer is neutralized by adding phase D. Phase E is then added under mild stirring and cooling is continued until 25° C. Phase F is then added if desired.

4—Protective Day Cream:

| Trade names | INCI names | Weight percent |
|---|---|---|
| Phase A | | |
| Emulium Delta | Cetyl alcohol (and) Glyceryl Stearate (and) PEG-75 Stearate (and) Ceteth-20 (and) Steareth-20 | 4.00 |
| Lanette O | Cetearyl Alcohol | 1.50 |
| D C 200 Fluid/100 cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| Cegesoft PS6 | Vegetable Oil | 1.00 |
| Vitamin E | Tocopherol | 0.30 |
| ROKONSAL MEP | Phenoxyethanol (and) Methylparaben (and) Ethylparaben (and) Propylparaben | 0.70 |
| Phase B | | |
| Demineralized water | Aqua | qsp 100 |
| Glycerin | Glycerin | 2.00 |
| Carbopol ETD 2020 | Acrylates/C10-30 Alkyl Acrylate Crosspolymer | 0.15 |
| Keltrol BT | Xanthan Gum | 0.30 |
| Phase C | | |
| Sodium Hydroxide (10% sol.) | Sodium Hydroxide | 0.30 |
| Phase D | | |
| Demineralized water | Aqua | 5.00 |
| Stay-C 50 | Sodium Ascorbyl Phosphate | 0.50 |
| Phase E | | |
| Butylene Glycol | Butylene Glycol | 2.00 |
| Dekaben CP | Chlorphenesin | 0.20 |
| Phase F | | |
| GP4G | Water (and) Artemia Extract | 1.00 |
| ACTIVE AGENT OF EXAMPLE 1 | | 0.001 |

Prepare phase A and heat to 75° C. under stirring. Prepare phase B by dispersing the carbopol and then the xanthan gum under stirring. Let rest. Heat to 75° C.

At 75° C., emulsify A into B under rotor stator stirring. At 60° C., neutralize with phase C under rapid stirring. After cooling to 40° C., add phase D, and then phase E (both homogenized until clear before). Cooling is continued under mild stirring and phase F is added.

The invention claimed is:

1. An aqueous Truffle extract for cosmetic treatment of skin and/or skin appendages, comprising compounds having a molecular weight of less than 5 kDa obtained from a fruiting body of *Tuber melanosporum* by aqueous extraction and enzymatic hydrolysis performed with enzymes selected from the group consisting of carbohydrases, proteases, and combinations thereof, wherein said enzymatic hydrolysis comprises multiple, sequential hydrolysis reactions, wherein a first hydrolysis reaction is conducted for between 1 and 2 hours at a temperature between 40 and 80° C. with between 1 and 10% of an enzyme complex comprising a carbohydrase enzyme, and then a second hydrolysis reaction is conducted for between 1 and 2 hours at a temperature between 40 and 80° C. with between 1 and 10% of an endoprotease enzyme.

2. The aqueous Truffle extract according to claim 1, wherein after the second enzymatic hydrolysis, a step of enzyme deactivation is carried out.

3. The aqueous Truffle extract according to claim 1, wherein said Truffle extract is diluted in a solvent selected from water, glycerol, ethanol, propanediol, butylene glycol, di propylene glycol, ethoxylated or propoxylated glycols, cyclic polyols or any mixture of these solvents.

4. A cosmetic composition comprising an aqueous Truffle extract comprising compounds having a molecular weight of less than 5 kDa obtained from a fruiting body of *Tuber Melanosporum* according to claim 1, and a physiologically acceptable medium.

5. The cosmetic composition according to claim 4, wherein said aqueous Truffle extract is used in a concentration from about 0.0001% by weight to about 20% by weight of the total weight of the composition.

6. The cosmetic composition according to claim 4, wherein said aqueous Truffle extract is used in a concentration from about 0.0005% by weight to about 5% by weight of the total weight of the composition.

7. The cosmetic composition according to claim 4, wherein said composition is topical composition.

8. The cosmetic composition according to claim 7, wherein said composition is in the form of a gel, a cream, a balm, a milk or a foaming product.

9. The cosmetic composition according to claim 4, further comprising at least one other active agent.

10. The cosmetic composition according to claim 9, further comprising at least one other active agent selected from the group consisting of an antioxidant agent, a hydrolysate of a plant, a synthetic peptide compound, a sunscreen, and an anti-wrinkle agent.

11. A method for reducing and/or correcting the signs of aging and photo-aging of the skin and keratinous appendages, comprising:
topically applying to the skin, the mucous membranes and/or superficial skin appendages a cosmetic composition according to claim 4.

12. The method according to claim 11, wherein reducing and/or correcting the signs of aging and photo-aging of the skin and keratinous appendages comprises protecting the skin against aggressions due to ultraviolet radiation.

13. The method according to claim 11, wherein reducing and/or correcting the signs of aging and photo-aging of the skin and keratinous appendages comprises increasing ATP levels in skin cells.

14. The method according to claim 11, wherein reducing and/or correcting the signs of aging and photo-aging of the skin and keratinous appendages comprises reducing Reactive Oxygen Species levels in skin cells.

15. The Truffle extract according to claim 1, wherein said first hydrolysis reaction is conducted for 2 hours at 55° C. with 4% of the enzymes complex comprising a carbohydrase including arabanase, a cellulase, a β-glucanase, a hemicellulase, and a xylanase or a beta glucanase extracted from yeast.

16. The Truffle extract according to claim 1, wherein said second hydrolysis reaction is conducted for 2 hours at 55° C. with 2% Bromelaine.

17. The Truffle extract according to claim 15, wherein the yeast is *Trichoderma harzianum*.

* * * * *